(12) United States Patent
Dimitrijevich et al.

(10) Patent No.: US 6,607,910 B1
(45) Date of Patent: Aug. 19, 2003

(54) TWO CHAMBER CELL CULTURE VESSEL

(75) Inventors: S. Dan Dimitrijevich, Bedford, TX (US); Charlie W. Dodd, Pasadena, TX (US); William J. Anderson, Richmond, TX (US); Ray P. Schwarz, Friendswood, TX (US)

(73) Assignee: Synthecon, Inc., Houston, TX (US)

( * ) Notice: Subject to any disclaimer, the term of this patent is extended or adjusted under 35 U.S.C. 154(b) by 166 days.

(21) Appl. No.: 09/711,458

(22) Filed: Nov. 13, 2000

(51) Int. Cl.[7] ............................................. C12M 1/12
(52) U.S. Cl. ........................... 435/297.1; 435/297.2; 435/298.2; 435/394; 435/401
(58) Field of Search ............... 435/297.1, 297.2, 435/297.5, 298.1, 298.2, 394, 395, 401–403

(56) References Cited

U.S. PATENT DOCUMENTS

| | | | | |
|---|---|---|---|---|
| 5,316,945 A | * | 5/1994 | Minuth | 435/297.3 |
| 5,459,069 A | * | 10/1995 | Palsson et al. | 435/289.1 |
| 5,602,028 A | * | 2/1997 | Minchinton | 435/401 |
| 6,008,049 A | * | 12/1999 | Naughton et al. | 435/395 |

* cited by examiner

*Primary Examiner*—David A. Redding
(74) *Attorney, Agent, or Firm*—John R. Casperson (57) ABSTRACT

A two-chamber perfusion bioreactor counteracts a significant amount of shear stress while allowing high nutrient transfer and removal of waste and/or valuable bio-products, e.g., protein, hormones, growth factors, and monoclonal antibodies without disturbing the cell culture. Cells and tissues, contained in the growth chamber, are suspended in the growth media by rotation of the vessel and are separated by a porous membrane from the feeding chamber. Nutrients and gases are transferred across the membrane from the feeding chamber to the growth chamber. Even dispersion of nutrients along the membrane barrier is accomplished through a novel nutrient dispersion flow path. The flow path is created by flowing media out a center shaft in the vessel and along the front of the nutrient dispersion disk. The fluid then flows around the back of the nutrient dispersion disk and exits the outer center return shaft. The feeding chamber can be constantly perfused with fresh media or recirculated to maintain constant concentration of a specific media or testing component, e.g., pharmaceutical drug test candidate, growth factor, or anti cancer compound. The two-chamber perfusion device allows the attachment of different types human cells to represent various tissues in the human body.

38 Claims, 5 Drawing Sheets

TWO CHAMBER CELL CULTURE VESSEL

BACKGROUND OF THE INVENTION

Historically, providing mama cell cultures with ideal growing conditions has been difficult. These delicate cells need low turbulence and high mass transfer of nutrients for proliferation and differentiation Bioreactors of the past have usually sacrificed one parameter for the other. Traditionally, stirring bars, bubble sparging and other mechanical means have promoted nutrient dispersion but also created significant shear stress and disruptive forces. Continuous shear stress causes the many cells to exit the proliferation or differentiation phases and activate survival mechanisms which may involve substantial cell death.

Another problem with current bioreactors is that there is no provision to separate the cells from the valuable bioproducts that they produce. Separating cells and cell debris from the secreted product is very labor intensive. Downstream processing costs account for roughly two-thirds of the manufacturing costs for secreted products.

A bioreactor to counteract a significant amount of shears stress while allowing high nutrient transfer and removal of waste and/or valuable bio-products, e.g., protein, hormones, growth factors, and monoclonal antibodies without disturbing the cell culture would be very desirable.

A bioreactor which provides a bioproduct in a near useable form would also be very desirable.

Another shortcoming of current technology is that there are no devices to test various drugs, agents, and compounds effectively against living barrier tissues or showing transmembrane dispersion of the drug, compound, or agent. An in vitro system for culturing a membrane bearing living tissue would be very desirable. A device to permit the testing of drugs against a living tissue barrier membrane would be very desirable. A device which permits the living tissue membrane to be easily replaced would be very desirable.

It would also be extremely desirable to manufacture a graftable human tissue, such as skin, in vitro. However, previous attempts have not been successful to meet this end. The provision of a graftable human tissue would be extremely desirable.

Rotating Vessels have been used in experimental programs to generate mono-cellular "organoids". In most experiments the "matrix" supporting the creation of three-dimensional architecture has been beads consisting of man made materials. The success always depended on the cells attaching efficiently to the beads and then being mitotically active enough to initiate aggregation of cell-covered beads. In successful experiments, the cells were generally immortal tumor cell lines and the objective was to create an in vitro model for studying efficacy of chemotherapeutic agents—anti-cancer drugs. For a number of years therefore very rarely were normal human cells cultured in the rotating vessels and never has a construction and maintenance of poly-cellular tissue such as might be useful for grafting been attempted. A living membrane of normal cells would be very desirable, especially one in the form of a cartridge which could be moved between bioreactors.

Further, although the tumoroids generated in vitro in rotating vessels were useful models to study anti-cancer therapies, since they mimicked an in vivo model better than the cell monolayers did, these organoids were more resistant to anti-cancer drugs or agents. It was also found that the cores in larger tumoroids were necrotic, suggesting that the large size "tissues" may not be receiving their required oxygen and nutrient concentrations. A device which can be used to grow usably sized living tissue would be very desirable.

SUMMARY OF THE INVENTION

A cell culture vessel comprising a front vessel half, a back vessel half, an inner tubular member, and a disk-shaped baffle is provided in one embodiment of the invention.

The front vessel half defines a front chamber. The back vessel half defines a back chamber which is generally cylindrical and has a longitudinal axis. The front vessel half is engageable with the back vessel half and comes together with the back vessel half so as to form an annular recess for receipt of a cylindrical sample cartridge rim of a sample cartridge which will separate the front chamber from the back chamber. The inner tubular member extends though an end wall of the back vessel half and into the back chamber along the longitudinal axis. The inner tubular member has an inner end which is positioned in the back chamber. The disk shaped baffle is mounted on the inner end of the tubular member and extends transversely across the back chamber so as to substantially form a partition across the back chamber. The baffle divides the back chamber into a front portion and a back portion. The inner tubular member forms a means for introducing fluid into the front portion of the back chamber. A means for withdrawing a fluid from the back portion of the back chamber is also provided. The invention can be used by positioning a layer of human cells or tissue on a permeable support and flowing culture medium across a cell surface defined by the layer of cells to provide the necessary nourishment.

In another embodiment of the invention, there is provided a sample cartridge which contains a connective tissue equivalent. The sample cartridge comprises a generally annularly shaped washer constructed of a polymeric material and having a first end face and a second end face, a semi-permeable membrane affixed to the first end face of the washer to form an end closure for a cell chamber defined inside of the washer, and a substrate of solidified collagen/fibroblasts mix layered on the semi-permeable membrane in the cell chamber to form the connective tissue equivalent. The sample cartridge can be used to grow epidermal or other types of cells, and can be used for cancer research as well as other types of research. A connective tissue equivalent can be formed with the just described sample cartridge by forming a substrate of solidified collagen/fibroblasts mix on the semi-permeable membrane in the cell chamber.

In another embodiment of the invention, there is provided a cell culture vessel which is useful for the generation of recombinant proteins, antibodies and other bioproducts, and in research. The vessel is formed from a front vessel half, a back vessel half, and a sample cartridge which separates the vessel halves to form two chambers. A growth of secretor cells is maintained in one chamber, while a means for collecting secretions, containing for example proteins, antibodies and other bio-products from the secretor cells, is maintained in a separated vessel chamber designed for collecting the secretions.

The front vessel half defines a front chamber. The back vessel half defines a back chamber which is generally cylindrical and has a longitudinal axis. The front vessel half is sealingly engageable with the back vessel half and comes together with the back vessel half so as to form an annular recess for receipt of a cylindrical sample cartridge rim. The sample cartridge rim is defined by a periphery of a sample cartridge which separates the front chamber from the back chamber. The sample cartridge is formed from a generally annularly shaped washer having a generally cylindrical cartridge rim, a first end face and a second end face. A semi-permeable membrane is affixed to the first end face of the washer and forms an end closure for a cell chamber defined inside of the washer. The sample cartridge is positioned in the cell culture vessel with the rim of the at least one generally cylindrical sample cartridge being positioned in the annular recess so as to separate the front chamber from the back chamber. The growth of secretor cells is maintained in one chamber while a means for collecting secretions from the secretor cells is maintained in the second chamber. The apparatus is preferably utilized by growing the secretor cells and collecting the secretions in adjoining chambers separated by a semi-permeable membrane cartridge.

DETAILED DESCRIPTION OF THE INVENTION

Figure 1:
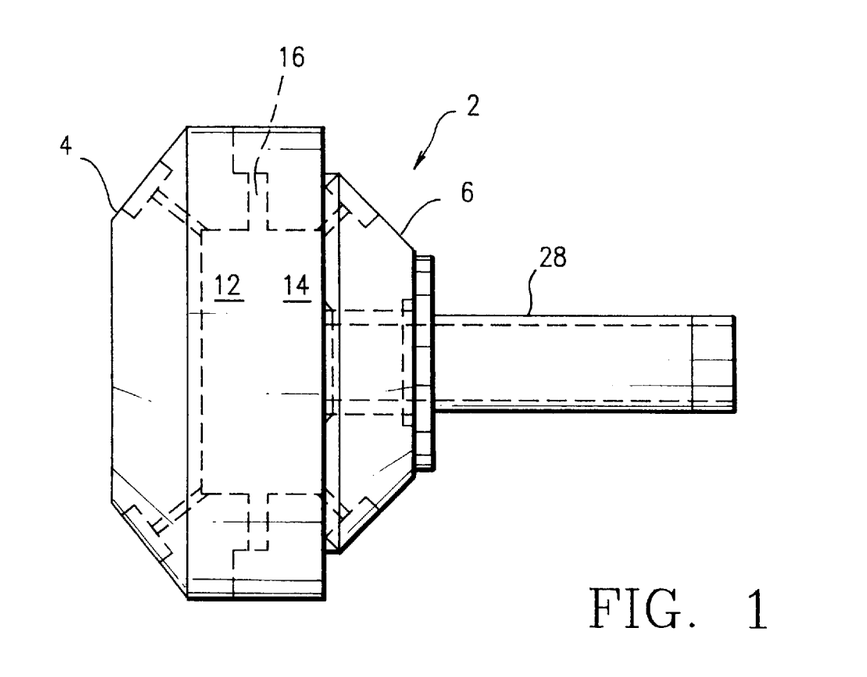
FIG. 1 is a cross sectional view of an apparatus illustrating certain features of the invention.

A cell culture vessel 2 comprising a front vessel half 4, a back vessel half 6, an inner tubular member 8, and a disk-shaped baffle 10 is provided in one embodiment of the invention.

Figure 8:
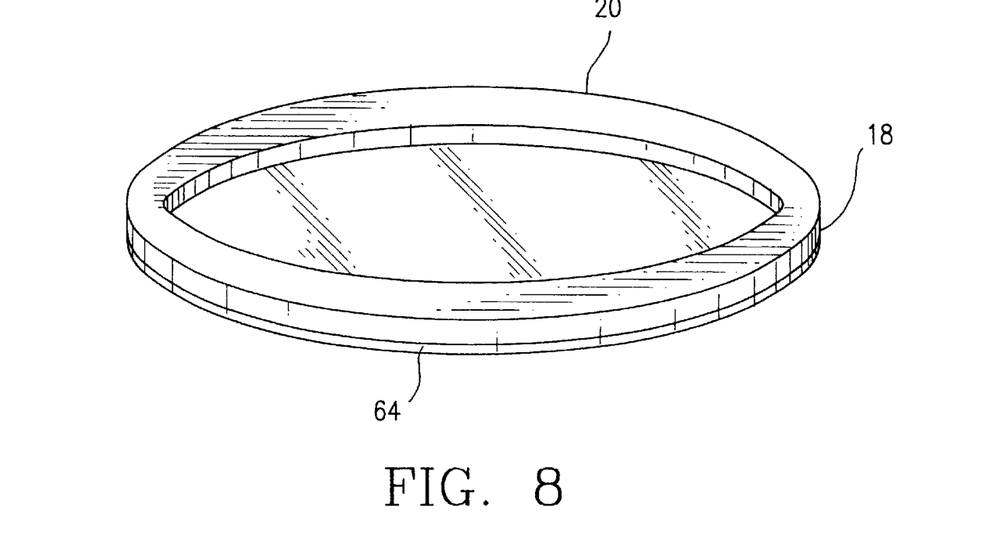
FIG. 8 is a pictorial representation of an inventive portion of the invention.

The front vessel half defines a front chamber 12. The back vessel half defines a back chamber 14 which is generally cylindrical and has a longitudinal axis. The front vessel half is engageable with the back vessel half and comes together with the back vessel half so as to form an annular recess 16 (see FIG. 1) for receipt of a cylindrical sample cartridge rim 18 (see FIG. 8) of a sample cartridge 20 which will separate the front chamber from the back chamber. The inner tubular member extends though an end wall of the back vessel half and into the back chamber along the longitudinal axis. The inner tubular member has an inner end which is positioned in the back chamber. The disk shaped baffle is mounted on the inner end of the tubular member and extends transversely across the back chamber so as to substantially form a partition across the back chamber. The baffle divides the back chamber into a front portion 22 and a back portion 24.

The inner tubular member forms a means for introducing fluid into the front portion of the back chamber. A means 26 (see FIG. 2) for withdrawing a fluid from the back portion of the back chamber is also provided.

Figure 2:
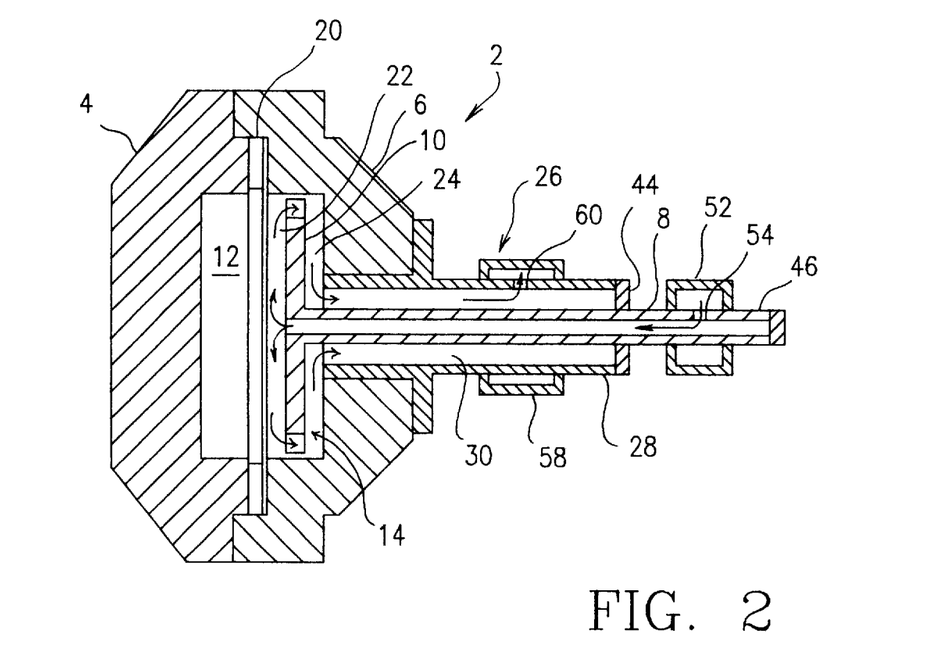
FIG. 2 is a cross section view of an apparatus illustrating certain additional features of the invention.
Figure 3:
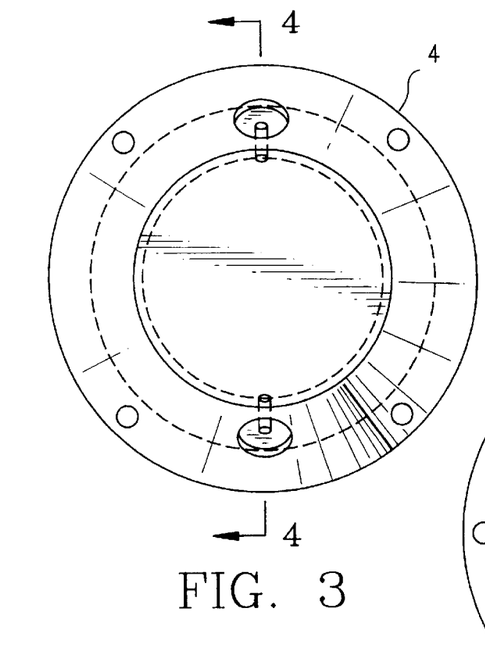
FIG. 3 is a first end view of a portion of the apparatus of FIG. 1.
Figure 4:
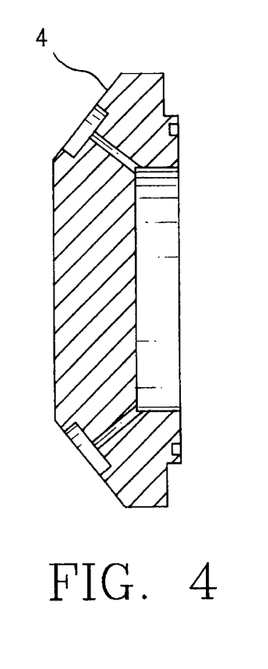
FIG. 4 is a cross sectional view of the portion of the apparatus shown in FIG. 3 taken along lines 4—4.
Figure 5:
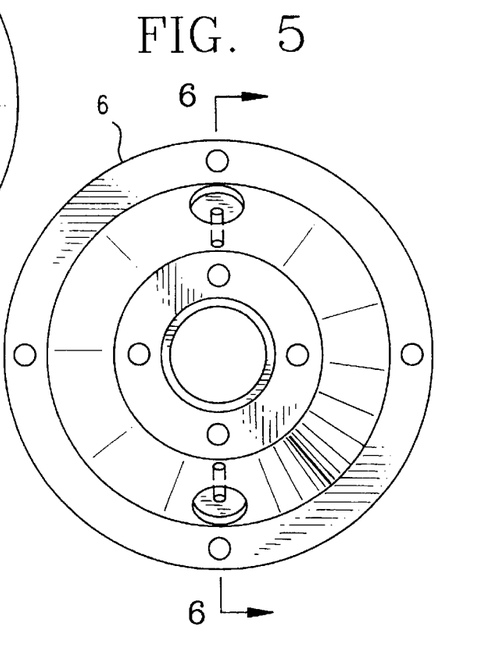
FIG. 5 is a second end view of a portion of the apparatus shown in FIG. 1.
Figure 6:
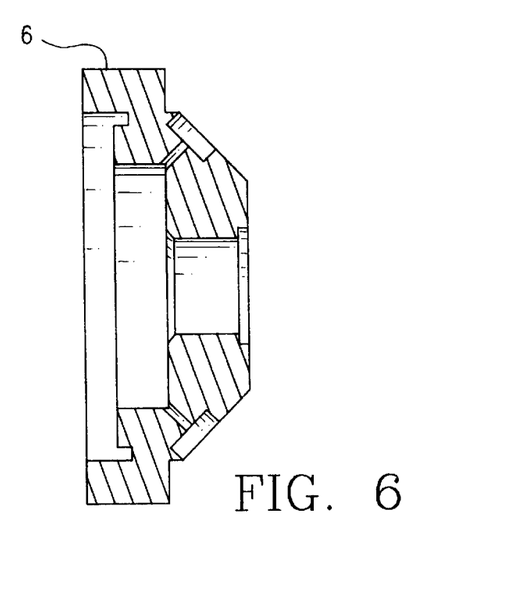
FIG. 6 is a cross sectional view of the portion of the apparatus shown in FIG. 5 taken along lines 6—6.

Preferably, the means for withdrawing fluid from the back portion of the back chamber comprises an outer tubular member 28 extending through the end wall of the back vessel half coaxial with the inner tubular member, an annular flow passage 30 being formed between the inner tubular member and the outer tubular member which opens into the back portion of the back chamber to permit the withdrawal of fluid.

Figure 9:
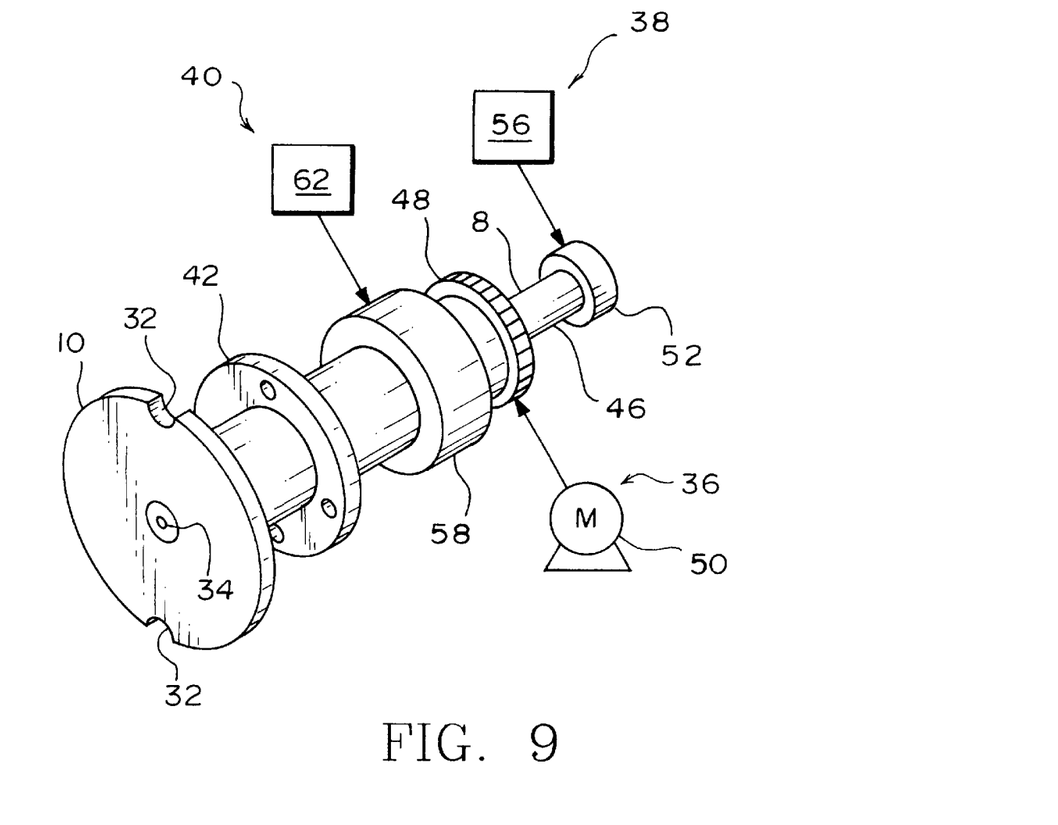
FIG. 9 is a pictorial representation, partly in schematic, of an inventive portion of the invention.
Figure 10:
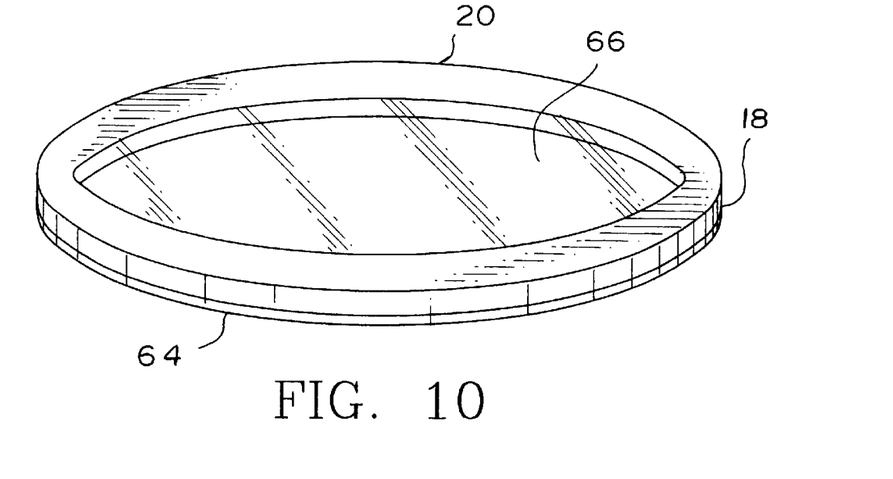
FIG. 10 is a pictorial representation of an inventive portion of the invention.

With reference to FIG. 9, the baffle preferably has a generally cylindrical outer periphery which is positioned closely adjacent to an inner wall of the back half of the vessel. The baffle preferably further defines a plurality of slots 32 on its outer periphery leading from the front portion of the back chamber to the back portion of the chamber to channel fluid flow from the front portion of the back chamber to the back portion of the back chamber. A nozzle 34 is preferably also positioned on the inner end of the inner tubular member.

In the illustrated embodiment, a rotation means 36 is provided for rotating the cell culture vessel about the longitudinal axis of the back chamber half Means 38 is provided for introducing fresh cell culture medium into the inner tubular member. Means 40 is provided for withdrawing spent cell culture medium from the outer tubular member.

Also shown in the illustrated embodiment, the outer tubular member is fixedly mounted to the back vessel half, such as by flange 42 and the inner tubular member is fixedly mounted to the outer tubular member, such as by flange 44 (see FIG. 2) and has an outer end portion 46 which protrudes beyond an outer end of the outer tubular member.

In a further preferred embodiment, the rotation means comprises a coupler 48 peripherally mounted to an outer surface of the outer tubular member outside of the back vessel half, and a motor 50 engaged with the coupler. The means for introducing fresh cell culture medium into the inner tubular member comprises an inner tubular member slip joint 52 rotatably mounted to an outer surface of the outer end portion of the inner tubular member in covering relationship with a transverse aperture 54 (see FIG. 2) defined by the inner tubular member. The inner tubular member slip joint defines a passage which is in flow communication with the transverse aperture defined by the inner tubular member, and a source 56 of fresh cell culture medium is in flow communication with the passage through the inner tubular member slip joint. The means for withdrawing spent cell culture medium from the outer tubular member comprises an outer tubular member slip joint 58 rotatably mounted to the outer surface of the outer tubular member outside of the back vessel half in covering relationship with a transverse aperture 60 (see FIG. 2) defined by the outer tubular member. The outer tubular member slip joint defines a passage which is in flow communication with the transverse aperture defined by the outer tubular member. A receptacle 62 for spent cell culture medium is in flow communication with the passage through the outer tubular member slip joint.

In use of the apparatus, the sample cartridge having a generally cylindrical sample cartridge rim positioned on an outer periphery is received by the annular recess. The sample cartridge separates the front chamber from the back chamber. The rim of the sample cartridge forms a generally annularly shaped washer having a first end face and a second end face and a semi-permeable membrane 64 (See FIG. 8) is affixed to the first end face of the washer to form an end closure for a cell chamber defined inside of the washer. The sample cartridge further comprises a colony 66 of living cells or living tissue attached to the semi-permeable membrane.

Figure 7:
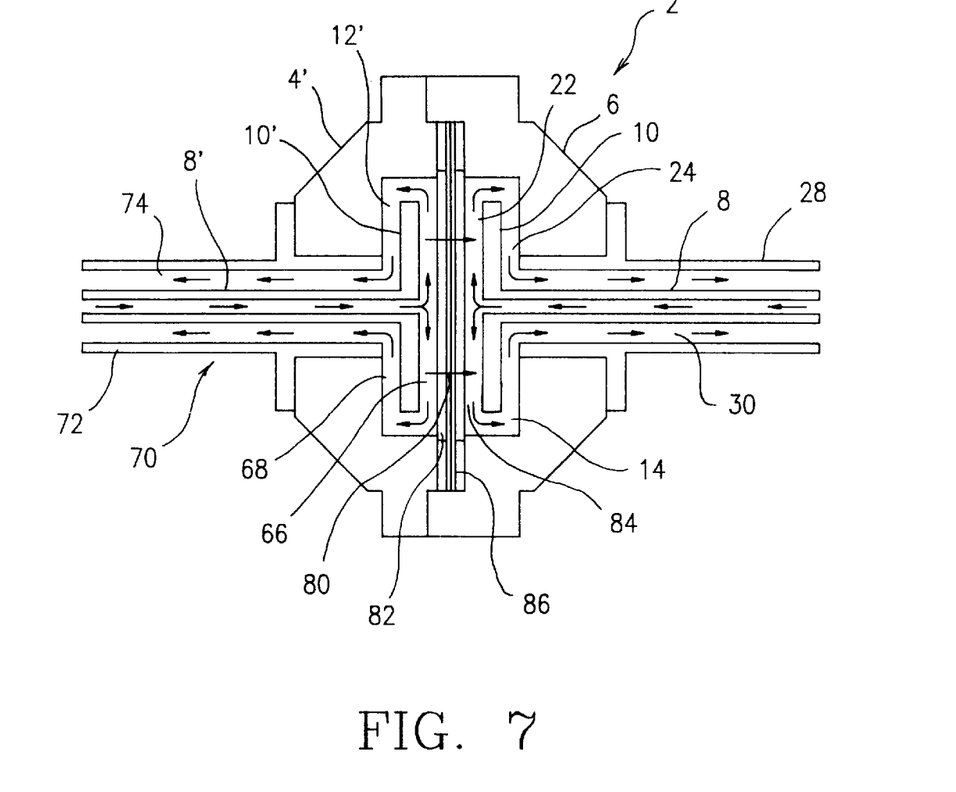
FIG. 7 is a cross sectional view of another embodiment of the invention.

In the embodiment of the invention illustrated in FIG. 7, the front chamber 12' is generally cylindrical and has a longitudinal axis. An inner tubular member 8' extends though an end wall of the front vessel half and into the front chamber along the longitudinal axis. An inner end of the inner tubular member is positioned in the front chamber. A disk shaped baffle 10' is mounted on the inner end of the inner tubular member and extending transversely across the front chamber so as to substantially form a partition across the front chamber. The baffle divides the front chamber into a front portion 66 and a back portion 68. The inner tubular member forms a means for introducing fluid into the front portion of the front chamber. Means 70 is provided for withdrawing a fluid from the back portion of the front chamber.

In the illustrated embodiment, the means for withdrawing fluid from the back portion of the front chamber comprises an outer tubular member 72 extending through the end wall of the front vessel half coaxial with the inner tubular member. An annular flow passage 74 is formed between the inner tubular member and the outer tubular member which opens into the back portion of the front chamber to permit the withdrawal of fluid.

The invention as described above can be used by positioning a layer of human cells or tissue on a permeable support and flowing culture medium across a cell surface defined by the layer of cells to provide the necessary nourishment. Generally speaking, the cell surface is vertically oriented and is rotated about a horizontal axis which is normal to the cell surface. The culture medium is flowed across the cell surface from a position on the horizontal axis. The culture medium is confined to flow in a path closely adjacent to the cell surface.

The cell surface can be described as forming an end of a generally cylindrical closed first chamber. The culture medium is directed away from the surface along a periphery of the first chamber. In using the embodiment of the invention shown in FIG. 7, the permeable support can be described as forming an end of a generally cylindrical closed second chamber. The method further comprises introducing a fluid into the second chamber which contains a component which can penetrate the permeable support. In the growing of human skin, for example, the human cells comprise epidermal cells and the fluid comprises air.

The invention provides a new two-chamber perfusion bioreactor to counteract a significant amount of shear stress while allowing high nutrient transfer and removal of waste and/or valuable bio-products, e.g., protein, hormones, growth factors, and monoclonal antibodies without disturbing the cell culture.

Cells and tissues, contained in the growth chamber, are suspended in the growth media by rotation of the vessel and are separated by a porous membrane (that could be of various pore sizes) from the feeding chamber. Nutrients and gases are transferred across the membrane from the feeding chamber to the growth chamber. Even dispersion of nutrients along the membrane barrier is accomplished through a novel nutrient dispersion flow path. The flow path is created by flowing media out a center shaft in the vessel and along the front of the nutrient dispersion disk. The fluid then flows around the back of the nutrient dispersion disk and exits the outer center return shaft. The feeding chamber can be constantly perfused with fresh media or recirculated to maintain constant concentration of a specific media or testing component, e.g., pharmaceutical drug test candidate, growth factor, or anti cancer compound.

Historically, a major deficiency of culture media is its inability to carry enough oxygen, because of the absence of hemoglobin, to maintain body-like levels of approximately 30–40 mm mercury PO2 in a tissue culture environment. It is contemplated that this limitation can be overcome by manipulating the pressure of the culture environment to force oxygen and other gases into the media, and/or by hyper-saturating the culture medium with gases such as in an external oxygenator.

The two-chamber perfusion device allows the attachment of different types human cells to represent various tissues in the human body. One normal cell type, which can synthesize an appreciable amount of matrix (collagen and glycosaminoglycans-GAGs), is cartilage cells-chondrocytes.

Preliminary experiments with conventional rotating vessels, such as the STLV or HARV, showed very quickly that the dynamic conditions provided by the rotation of the vessel did not allow the collagen to gel and the connective tissue equivalent could not be set up in the traditional way. The vessels were modified by machining four compartments in the base of the vessel or the vessel cylinder wall These were filled with collagen/fibroblasts mix, allowed several hours to solidify (gel) and then filled with medium and set to rotate. The rotation is initiated before the cells have the opportunity to stretch out and adapt to the collagen matrix. Although both configurations work, the configuration with the compartments machined into the base is the preferred configuration because the four compartments can be set simultaneously. It is therefore quicker and more efficient method for initiating four repeats of the connective tissue equivalent.

The next phase in the skin equivalent construction is generation of the epidermis. The medium is removed from the DE and after a brief period of drainage of medium from the surface (about 1 hour) the dermal equivalent can be coated with a basement membrane component (collagen type IV or laminin) and the coating allowed to adhere to the surface of the DE. Thereafter early passage normal human keratinocytes (the principle epidermal cell type) are plated on the surface of the coated DE. After a period of attachment (at least 8 hours) the vessel is again set into rotation and the cells allowed to form a confluent monolayer. Seeding density of the keratinocytes can be adjusted so that either the confluent monolayer is formed without the need for cell division or the cells are allowed to proliferate and form a confluent monolayer.

The next phase in the generation of the Skin Equivalent (SE), which is applicable to stratified epithelia only, is differentiation and formation of the full thickness cornified epidermis. This can only take place by culturing the model at the air-liquid interface. Since the rotating vessel is normally used with the complete exclusion of air, a further modification of the vessel had to be instituted in order to allow the presence of the air-liquid interface. This requirement was satisfied by the construction of a double chambered vessel according to the embodiments of the invention. In this vessel the compartment on one side of the dermal equivalent can hold the medium while the medium can be removed from the compartment on the epidermal side of the DE thus allowing the keratinocytes to differentiate and cornify. The tissue equivalent (SE in this case) is generated as a cartridge at the junction of the two chambers and in a series of wells, which have a semipermeable membrane separating the two chambers of the vessel.

The Human Skin Equivalent generated in this type of a "system" can be used to study the effect of "hostile environment" on this complex barrier tissue. The hostile elements of the environment can be:

1. Corrosive airborne chemicals, aerosols or liquids; model can be used to assess the effect of acute or chronic exposures and the efficacy of preventive or protective measures.
2. Infectious microorganisms (viruses, bacteria, fungi); model can be used to study mechanisms of infection, ability to harbor the infective agent, recovery after the infection and the efficacy of curative or protective agents (e.g., bacteriostatic and bactericidal agents).
3. Induction of squamous cell and basal cell carcinoma, after UV exposure alone or in combination with other carcinogens. The efficacy of UV blocking agents and anticancer therapies. Addition of melanocytes to the skin equivalent can further extend its utility to studies of development of melanomas.
4. The effect of radiation generated by decay of radioisotopes and prevention of the same, cosmic radiation (space exploration).
5. The presence of novel microorganisms encountered during space explorations or novel biological warfare agents.
6. Skin irritation index of pharmaceuticals and consumer products.

The methodology would decrease the use of animals in research.

In addition to the generation of the Skin Equivalent this vessel is equally suitable for culturing any other stratified surface epithelia such those present in the cornea, conjunctiva, vagina, and cervix. The mid-vessel divider containing the tissue equivalents is in fact a removable biological cartridge.

Thus according to another embodiment of the invention, there is provided a sample cartridge which contains a connective tissue equivalent. The sample cartridge comprises a generally annularly shaped washer constructed of a polymeric material and having a first end face and a second end face, a semi-permeable membrane affixed to the first end face of the washer to form an end closure for a cell chamber defined inside of the washer, and a substrate of solidified collagen/fibroblasts mix layered on the semi-permeable membrane in the cell chamber to form the connective tissue equivalent. The sample cartridge can be used to grow epidermal or other types of cells, and can be used for cancer research as well as other types of research.

In further embodiments, the sample cartridge can further comprise a coating of a basement membrane component coated on the connective tissue equivalent and forming a coated connective tissue equivalent. The basement membrane component can be selected from the group consisting of collagen type IV or laminin. Normal human keratinocytes can be plated on the surface of the coated connective tissue equivalent. The keratinocytes preferably form a confluent monolayer. For the skin model, the keratinocytes are preferably further characterized as differentiated and cornified.

Different epitheliums can be coated on the connective tissue equivalent. For example, human conjunctival epithelium, human vaginal epithelium, human cervical epithelium, human oral cavity epithelium, human bronchial airway epithelium, human intestinal epithelium, human colon epithelium, human urinary tract epithelium, and human bladder epithelium can all be coated on the connective tissue equivalent and studied or cultivated for grafting. The invention is used to provide stratified epithelia by first forming a substrate of solidified collagen/fibroblasts mix on the semi-permeable membrane in the cell chamber of the sample cartridge to provide the connective tissue equivalent. The steps to provide the specific epithelium are carried out. For example, a coating of a basement membrane component on the connective tissue equivalent to form a coated connective tissue equivalent can be carried out. The basement membrane component can be selected from the group consisting of collagen type IV or laminin. Normal human keratinocytes can then be plated on the surface of the coated connective tissue equivalent, preferably as a confluent monolayer. For the skin model, the keratinocytes are then caused to become differentiated and cornified by exposure to air.

Figure 11:
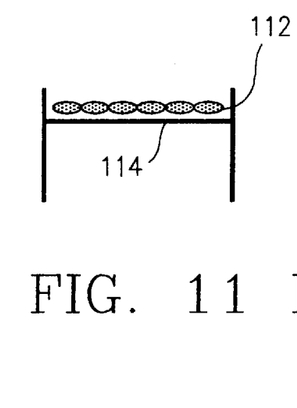
FIGS. 11–19 illustrate schematically various sample cartridge lay ups constructed according to embodiments of the invention.
Figure 12:
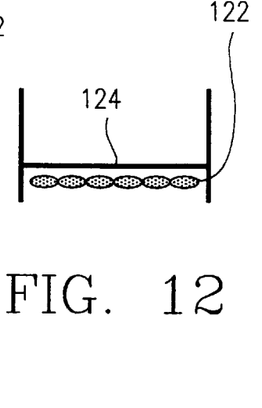
Figure 16:
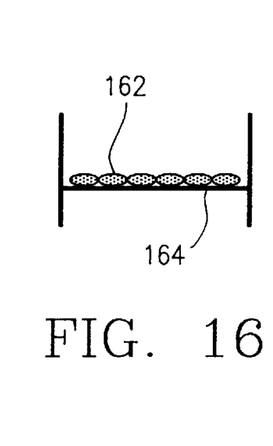

FIGS. 11, 12, and 16 show a monolayer of cells 112, 122, and 162, respectively (for example, epithelial or endothelial) on a semipermeable membrane 114, 124, 164, respectively. This format in Rotating Vessel could produce a cartridge that could be used for evaluation of cell attachment and growth and the substances or conditions that would augment this growth or attachment. In secreting epithelial cells the cartridge could be used to extend capabilities into studies of secretion process/mechanisms. In endothelial cells permeability of the monolayer to other cells or substances or modulation of this permeability could be studied.

Figure 13:
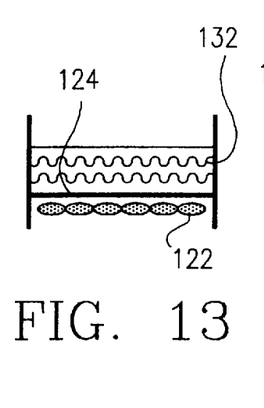
Figure 14:
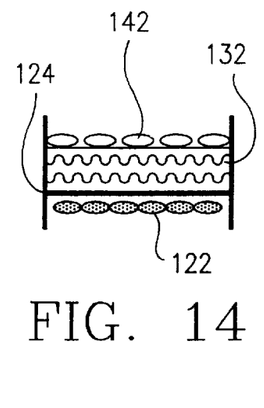
Figure 17:
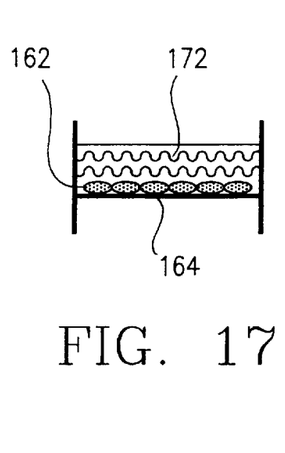
Figure 18:
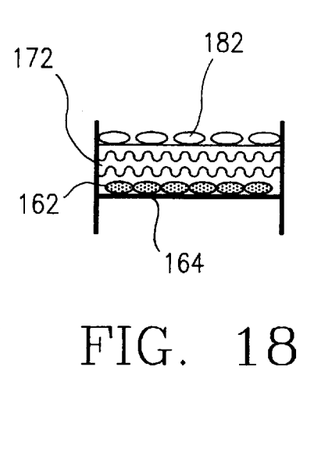

The lay ups shown in FIGS. 13 and 17 illustrate an intermediate configuration toward the production of the cartridges shown in FIGS. 14 and 18 from those shown in FIGS. 12 and 16, respectively. Both could be used to study the effect of an "overlay" of matrix 132, 172 (for example, collagen) on the cells that would be covered (cell-matrix interactions). For example, the behavior of cancer cells (or even some normal cells) could be studied to determine whether they have the ability to move through the matrix in response to a chemotactic signal, or whether the cells secrete when covered with an appropriate matrix.

In FIGS. 14 and 18, a single layer of epithelial cells 142, 182 is generated to simulate a tissue situation. This could be used for evaluation of attachment of cells to and propagation on the matrix under the influence of another one or two additional cell types. Collagen could be acellular (containing no cells), populated with fibroblasts, or populated with any other cell types which would be appropriate according to what type of tissue is being simulated. This configuration could be used to study secretion, exposure to microbial infective agents, and prevention of infectious diseases.

Figure 15:
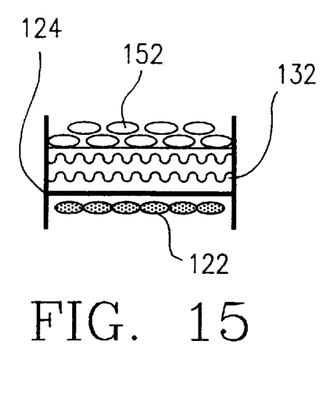
Figure 19:
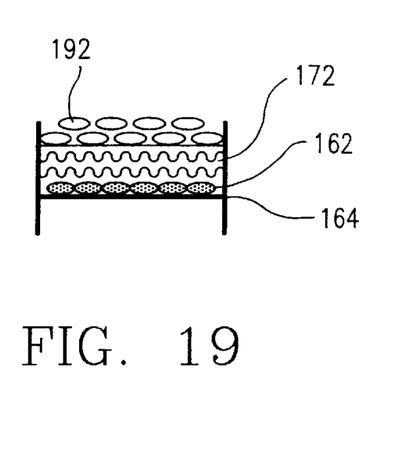

FIGS. 15 and 19 represent a tri-cellular model with a filly stratified epithelium 152, 192. This could be used as full model of tissues such as cornea, conjunctiva, skin, cervical or vaginal epithelium. Studies relating to trans-epithelial transport, mechanism of infection due to microbial agents (bacteria, viruses, fungi), carcinogenesis, radiation and environmental pollutants (chemicals and gases) consumer products, topical pharmaceuticals, or cosmetics could be performed with this configuration. This configuration could also be used to prepare tissue grafts for tissue replacement therapy, targeted delivery of growth factors producing or otherwise genetically engineered cells. Strategies for producing graft tissue composed of genetically altered cells could also be studied using this approach.

The Corneal Epithelial Equivalent, being also a very effective barrier tissue model can be challenged with the same type of agents, with the possible exception of carcinogenesis since there have been no documented cases of corneal cancers.

The conjunctiva is a unique eye tissue which is very sensitive to allergens and inflammatory agents; The Conjunctival Epithelial Equivalent therefore would be very useful in studying ocular allergy and inflammation and evaluating anti-allergy and anti-inflammatory drugs. Furthermore, since conjunctival epithelium is a mucous secreting epithelium, and the model contains mucous producing goblet cells, it can be useful for studying "dry eye" syndromes.

The Vaginal Epithelial Equivalent can be utilized in studies on effect of hormonal changes, the studies of infectious agents, particularly STDs, the effect of nutrition on internal pH (which can contribute to infection), and the efficacy of anti-infective agents. Since this is also a mucous producing epithelium, the model can be useful for studying disorders (some age related) which result in reduction or loss of mucous production and ensuing consequences (infections, irritation and pain).

The Cervical Epithelial Equivalent can be utilized in studying responses to hormonal changes, microbial infections (STDs) and carcinogenesis, efficacy of preventive measures and drugs to fight the damage caused by STDs.

All of the above epithelia can be generated in the two-chamber vessel with or without the underlying connective tissue equivalent. A unicellular version of the model (epithelial cells only) would also be useful in some aspects of the above-mentioned strategies and can be utilized in Phase I and Phase II in vitro strategies which are described as follows. Phase I would employ a monolayer of epithelial cells. Phase II would employ a stratified multi-layer epithelium. Phase III would include advanced studies in which the epithelium is differentiating on the connective tissue equivalent, as would be encountered with an epithelium which is recovering from injury. Phase IV would be the model of the intact fully functional differentiating epithelium on the connective tissue equivalent.

In addition to the stratifying epithelium many internal body surfaces such as the oral cavity, respiratory system (bronchial airways), digestive tract (intestinal epithelium) and the colon, urinary tract and the bladder etc. are lined with a single layer of epithelial cells which serve not only as a barrier tissue but also fulfil secretory or absorptive functions. Clearly these can also be cultured in the two-chamber vessel. In some cases (e.g., bronchial airway) an air-liquid interface for differentiation into functional phenotypes is required. Although the bronchial epithelial airway epithelial cells have already been cultured in a two-chamber vessel, further development of other cellular models, such as of the gut, is of very acute interest.

In other cases, culturing in the two-chamber vessel is the only in vitro method of simulating dynamic in vivo environment. Such is the case of the gut in which different parts of the digestive tract duodenum ileum and jejunum are lined with different epithelia with different pH tolerances and absorptive and secretory properties. These cells are also involved in the break down of food and absorption of various nutrients.

The digestive tract is a vital pharmacological compartment because the vast majority of pharmaceuticals are ingested orally and have to retain their bio-availability and enter the blood stream within the targeted compartment of the gut. Since these are substances foreign to these tissues they can, and often do, cause irritation, which can severely upset the balance of transport of nutrients and water across the intestinal epithelia. Serious general irritation can cause vomiting or diarrhea and lead to dehydration. Highly localized irritation can lead to ulceration and bleeding. It has to be realized intestinal epithelial turnover is about 48 hours and that disruption of the balanced turnover leads to an increased exposure of the unprotected intestinal wall (exposing vasculature and innervation) and escalation of damage and inflammation.

In addition to drug irritation, intestinal disorders such as chronic ulcerative colitis (Chrone's Disease) pose questions which can only be addressed by a better understanding of the functions of the intestinal epithelia system.

The most recent perfused version of the two-chamber vessel was developed for the purposes of developing models of the three compartments of the gut. As was explained earlier the simplest format of the biocellular cartridge will consist of the intestinal epithelial cells from the duodenum ileum and jejunum. The escalation of complexity would include the underlying connective tissue equivalent to represent the intestinal wall.

In another embodiment of the invention, there is provided a cell culture vessel which is useful for the production of recombinant proteins, antibodies and other bioproducts. The vessel is formed from a front vessel half, a back vessel half, and a sample cartridge which separates the vessel halves to form two chambers. A growth of secretor cells is maintained in one chamber, while the other chamber provides a means for collecting secretions from the secretor cells.

The front vessel half defines a front chamber. The back vessel half defines a back chamber which is generally cylindrical and has a longitudinal axis. The front vessel half is sealingly engageable with the back vessel half and comes together with the back vessel half so as to form an annular recess for receipt of a cylindrical sample cartridge rim. The sample cartridge rim is defined by a periphery of a sample cartridge which separates the front chamber from the back chamber. The sample cartridge is formed from a generally annularly shaped washer having a generally cylindrical cartridge rim, a first end face and a second end face. A semi-permeable membrane is affixed to the first end face of the washer and forms an end closure for a cell chamber defined inside of the washer. The sample cartridge is positioned in the cell culture vessel with the rim of the at least one generally cylindrical sample cartridge being positioned in the annular recess so as to separate the front chamber from the back chamber. The growth of secretor cells is maintained in one chamber while a means for collecting secretions from the secretor cells is maintained to collect the secretions. This aspect of the invention can be carried out in the embodiment shown in FIG. 7, for example.

In one embodiment, the semi permeable membrane has pores sized to permit the passage of secretions and prevent the passage of the secretor cells and the secretions are collected in the other chamber. Flow of the desired sections can be across the membrane(s) as illustrated by arrow 80. For example, the secretor cells 82 can comprise metastasizing tumor cells and the means for collecting secretions can comprise target cells 84 in the other chamber. In another embodiment, the secretor cells can comprise metastasizing tumor cells and the semi permeable membrane 86 carries a reactive agent for selectively binding a chemoattractant stimulating metastasis of the metastasizing tumor cells. In another embodiment, the secretor cells can comprise metastasizing tumor cells and the semi permeable membrane 86 can carry a reactive agent to prevent migration of the metastatic cells into the other chamber. In yet another embodiment, a chemoattractant substance on the semi-permeable membrane 86 is employed to bind with secretions from the secretor cells.

The apparatus is used by growing the secretor cells in one chamber and collecting the secretions at some other location in the reactor.

There are several other applications of the two-chamber vessel, which are unrelated to generation of tissue equivalent models but which are also of high importance.

The two chamber vessel can easily be adapted for the growth of secretor cells in one chamber while the secreted protein can be collected from the second chamber. The dividing membrane can be selected to allow only the passage of the macromolecules the size of the recombinant protein (molecule) or can be so treated to bind the recombinant protein. The desired molecule, in pure form, can then be removed (displaced) from the membrane. The membrane also keeps the cells from contaminating the secreted molecules they produce. Such a system can be set up as a continuous process that would operate well at zero gravity on the Space Station. Since crystallization of proteins (enzymes, drug receptor complexes) is relatively easy at zero gravity, and this is a part of NASA Program that is commercially rewarding, a continuous process of this would be very useful. A specific example of this type of application would be production of monoclonal antibodies.

An in vitro situation can be set up in the apparatus of the invention in which one side of the vessel contains tissue from a metastasizing tumor while the other contains a potential target tissue (s). The medium filling the vessel would be such that it supports the viability of both tissues. The tissue can be immobilized in the compartments with plastic mesh, large pore membrane or be embedded in collagen type I matrix (gel). The membrane dividing the two chambers can be such that it selectively binds a chemoattractant stimulating the metastasis in which case the experiments would lead to identification and quantitation of such entity(s). Alternatively substances that are potential anti-metastatic agents can be tested for efficacy in the system. A third case scenario would be to make the membrane discriminate between metastatic and non-metastatic cells (for example on the basis of their surface markers) and thereby prevent cell migration from the tumor to the target tissue. It is easily conceivable that individualizing these events to a specific patient would be simple using this methodology and arrive at a special treatment protocol for each cancer patient.

Further, for certain embodiments of the invention, it is preferred to use a non-contracting tissue equivalent in the rotating vessel. Such equivalent is described in co-pending application Ser. No. 09/046,755 filed Mar. 24, 1998, now abandoned, the disclosure of which is incorporated by reference.

A non-contracting tissue equivalent means that the collagen/fibroblast mix when poured into any receptacle retains its original dimensions and does not spontaneously shrink—contract. The advantages of the non-contracting tissue equivalent are that it is translucent, enabling one to observe cells within it by simple light or fluorescence microscopy and that it resembles normal tissue in development in that it can become vascularized and innervated very easily and can better support epithelia because it allows better diffusion of nutrients. Contracted equivalents are opaque and dense tissue, more like scar tissue than normal tissue. It is difficult to vascularize and innervate and support normal epithelium with this material.

EXAMPLES

General

The methodology will be described for preparation of an epithelial cell monolayer, a stratified epithelium differentiated at the air liquid interface, a monolayer epithelium as would represent the model of the gut (including the intestinal wall), and a skin equivalent as the model with both the dermal equivalent and the fully stratified epithelium differentiated at the air-liquid interface.

Example 1

The Epithelial Monolayer (Intestinal Epithelium Model)

The membrane used as the "divider" to create (define) the two chamber vessel is generally a man made polymer material with certain pore size. The pore size in this example should be large enough to allow the passage of nutrients but prevent migration of the cells through it. This membrane is attached to the vessel (sterile silicone adhesive) and one surface is then coated with a basement membrane component, usually fibronectin (FNC from BRFF) but collagen type IV or laminin is preferred (0.5–10 $\mu g/cm^{2-}$, from Collaborative Res.). The coating is allowed to adhere to the membrane (FNC is used, wet collagen IV and laminin have to dry under sterile conditions) and the epithelial cells (20,000/100,000/cm$^2$) are then plated on the coated surface of the membrane and allowed to attach (2–8 hours) in the presence of low calcium (<0.09 mM), serum free defined medium (2–10 mls) (usually KGM from Clonetics-Bio Whittaker, but Epilife from Cascade Biologicals or Sigma is preferred). The vessel is then assembled and the system charged with the same serum free defined medium free of air bubbles and set to rotate under perfusion conditions. The cells are then cultured until a confluent monolayer of cells is established on the membrane (cartridge). The cartridge can be removed to confirm confluence by labeling the cells with general or specific markers and viewing by light or fluorescence microscopy. This procedure has to be carried out under sterile conditions and without undue mechanical stress to prevent contamination and loss of cells, respectively. When serial experiments are planned, either a multiple vessel system can be used or the cartridge can be generated in advance outside the vessel since the attachment step does not involve rotation.

Example 2

The Stratified-Multilayered Epithelium

The initial stage of the process is identical to the one described for the single layer epithelium to the point when the confluent monolayer is generated. Thereafter medium from the chamber on the cell side of the membrane is removed and this chamber now provides the air necessary to stimulate cell differentiation and results in formation of the stratified epithelium. In order to facilitate the process of differentiation calcium concentration in the medium circulating in the other chamber has to be increased (0.5–1.8.mM). This can be accomplished by introducing the calculated amount of sterile concentrated stock of calcium chloride (10 mM). The cell side chamber is also kept damp with this high calcium defined medium (1–2 mls). The vessel is rotated until full uniform stratification is achieved as shown by increasing opacity of when the cell layer is examined by light microscopy under sterile conditions. Depending on epithelium, the time for differentiation to be completed will vary from 10 days (corneal epithelium) to 21 days (skin epithelium—epidermis). Thereafter the cartridge is ready for further experimentation. If two electrodes are included in the vessel one on either side of the membrane, the increase in trans-epithelial resistance will be a measure of the epithelial integrity and maximal resistance indicates uniform stratification.

Example 3

Full Gut Model

Intestinal connective tissue cells, harvested from cell number expansion experiments, are dispersed in a solution of collagen type I (3 mg/ml, 8 parts), F12 medium (10X, 1 part) and reconstitution buffer (200 mM HEPES, 25 mM $Na_2CO_3$, 50 mM NaOH, 1 part) at 4° C. so that the final cell population is 100–500,000 cells/ml. This mixture is introduced into the vessel by pipetting onto the top surface of the dividing membrane, and allowed to gel at 37° C. under sterile conditions. After several hours (4–18) warm (37° C.) medium (modified F12 with 5% fetal bovine serum) is carefully added to the vessel and the vessel set to rotate. Such a connective tissue equivalent when supplied with sufficient nutrients and adequate oxygenation has been sustained in the rotating vessels for up to one month without the loss of viability. The equivalent when treated as described above does not contract unless induced to and remains translucent so that the cells contained therein are easily discernable by light microscopy.

In the second phase the medium is removed from the chamber facing the equivalent and the equivalent coated under sterile conditions with basement membrane components fibronectin mix (FNC), but preferably collagen type IV or laminin as previously described in Example 1. The intestinal epithelial cells, (from duodenum, ileum or jejunum), are then plated on the coated surface of the connective tissue equivalent at a cell density of 100,000–500,000 cell/$cm^2$ and allowed to attach without rotation (see Example 1 above). The chamber of the vessel is the filled with low calcium, serum free defined medium (KGM, but Epilife preferred) and the vessel set to rotate. When the cells are confluent as determined by light or fluorescence microscopy and labeled with general or specific markers the model is ready to be used in further experiments.

Example 4

The Full Skin Equivalent

The dermal equivalent is prepared using similar methodology described in Example 3 except that normal human dermal fibroblasts, major cell type found in the human dermis, are used to populate the collagen type I gel and produce the Dermal Equivalent.

The second phase is similar to that in Example 3 above except that the normal human keratinocytes, the principle epithelial cell type of the human epidermis, is plated on the surface of the Dermal Equivalent. The epidermal layer is determined to be confluent as described in previous Examples above, and the chamber was emptied of medium and a small amount (up to 500 µL) of the defined medium (KGM but preferably Epilife) containing high calcium is allowed to come in contact with the cells. The vessel is then set into rotation and the differentiation process allowed to proceed at the air liquid interface for 14–21 days. The model is then ready for use in further experiments.

What is claimed is:

1. A cell culture vessel comprising a front vessel half which defines a front chamber, a back vessel half which defines a back chamber, said back chamber being generally cylindrical and having a longitudinal axis, said front vessel half being sealingly engageable with the back vessel half and coming together with said back vessel half so as to form an annular recess for receipt of a cylindrical sample cartridge rim defined by a periphery of a sample cartridge to separate the front chamber from the back chamber, an inner tubular member extending though an end wall of the back vessel half and into the back chamber along the longitudinal axis thereof, said inner tubular member having an inner end positioned in the back chamber, a disk shaped baffle mounted on the inner end of the tubular member and extending transversely across the back chamber so as to substantially form a partition across the back chamber, said baffle dividing the back chamber into a front portion and a back portion, wherein the inner tubular member form a means for introducing fluid into the front portion of the back chamber, and a means for withdrawing a fluid from the back portion of the back chamber.

2. A cell culture vessel as in claim 1 wherein the means for withdrawing fluid from the back portion of the back chamber comprises an outer tubular member extending through the end wall of the back vessel half coaxial with the inner tubular member, an annular flow passage being formed between the inner tubular member and the outer tubular member which opens into the back portion of the back chamber to permit the withdrawal of fluid.

3. A cell culture vessel as in claim 2 wherein the baffle has a generally cylindrical outer periphery which is positioned closely adjacent to an inner wall of the back half of the vessel, said baffle further defining a plurality of slots on its outer periphery leading from the front portion of the back chamber to the back portion of the chamber to channel fluid flow from the front portion of the back chamber to the back portion of the back chamber.

4. A cell culture vessel as in claim 3 further comprising a nozzle positioned on the inner end of the inner tubular member.

5. A cell culture vessel as in claim 4 further comprising rotation means for rotating the cell culture vessel about the longitudinal axis of the back chamber half, means for introducing fresh cell culture medium into the inner tubular member, and means for withdrawing spent cell culture medium from the outer tubular member.

6. A cell culture vessel as in claim 5 wherein the outer tubular member is fixedly mounted to the back vessel half and the inner tubular member is fixedly mounted to the outer tubular member and has an outer end portion which protrudes beyond an outer end of the outer tubular member.

7. A cell culture vessel as in claim 6 wherein the rotation means comprises a coupler peripherally mounted to an outer surface of the outer tubular member outside of the back vessel half, and a motor engaged with the coupler, the means for introducing fresh cell culture medium into the inner tubular member comprises an inner tubular member slip joint rotatably mounted to an outer surface of the outer end portion of the inner tubular member in covering relationship with a transverse aperture defined by the inner tubular member, said inner tubular member slip joint defining a passage therethrough in flow communication with the transverse aperture defined by the inner tubular member, and a source of fresh cell culture medium in flow communication with the passage through the inner tubular member slip joint;

and the means for withdrawing spent cell culture medium from the outer tubular member comprises an outer tubular member slip joint rotatably mounted to the outer surface of the outer tubular member outside of the back vessel half in covering relationship with a transverse aperture defined by the outer tubular member, said outer tubular member slip joint defining a passage therethrough in flow communication with the transverse aperture defined by the outer tubular member, and a receptacle for spent cell culture medium in flow communication with the passage through the outer tubular member slip joint.

8. A cell culture vessel as in claim 7 further comprising a sample cartridge having a generally cylindrical sample cartridge rim positioned on an outer periphery thereof received by the annular recess, said sample cartridge separating the front chamber from the back chamber.

9. A cell culture vessel as in claim 8 wherein the rim of the sample cartridge forms a generally annularly shaped washer having a first end face and a second end face and a semi-permeable membrane is affixed to the first end face of the washer to form an end closure for a cell chamber defined inside of the washer.

10. A cell culture vessel as in claim 9 wherein the sample cartridge further comprises a colony of living cells attached to the semi-permeable membrane.

11. A cell culture vessel as in claim 1 wherein the front chamber is generally cylindrical and has a longitudinal axis, said apparatus further comprising an inner tubular member extending through an end wall of the front vessel half and into the front chamber along the longitudinal axis thereof, said inner tubular member having an inner end positioned in the front chamber, and a disk shaped baffle mounted on the inner end of the inner tubular member and extending transversely across the front chamber so as to substantially form a partition across the front chamber, said baffle dividing the front chamber into a front portion and a back portion, wherein the inner tubular member form a means for introducing fluid into the front portion of the front chamber, and a means for withdrawing a fluid from the back portion of the front chamber.

12. A cell culture vessel as in claim 11 wherein the means for withdrawing fluid from the back portion of the front chamber comprises an outer tubular member extending through the end wall of the front vessel half coaxial with the inner tubular member, an annular flow passage being formed between the inner tubular member and the outer tubular member which opens into the back portion of the front chamber to permit the withdrawal of fluid.

13. A method for growing human cells, said method comprising positioning a layer of human cells on a permeable support, said layer having a cell surface, and flowing culture medium across the cell surface to nourish the cells, wherein the cell surface is vertically oriented and is rotated about a horizontal axis which is normal to the cell surface, and the culture medium is flowed across the cell surface from a position on the horizontal axis, wherein the culture medium is confined to flow in a path adjacent to the cell surface, and wherein the cell surface forms an end of a generally cylindrical closed first chamber, said method further comprising directing culture medium away from the surface along a periphery of the first chamber.

14. A method as in claim 13 wherein the permeable support forms an end of a generally cylindrical closed second chamber, said method further comprising introducing a fluid into the second chamber which contains a component which can penetrate the permeable support.

15. A method as in claim 14 wherein the human cells comprise epidermal cells and the fluid comprises air.

16. A cell culture vessel comprising a front vessel half which define a front chamber, a back vessel half which defines a back chamber, said back chamber being generally cylindrical and having a longitudinal axis, said front vessel half being sealingly engageable with the back vessel half and coming together with said back vessel half so as to form an annular recess for receipt of a cylindrical sample cartridge rim defined by a periphery of a sample cartridge to separate the front chamber from the back chamber, at least one sample cartridge formed from a generally annularly shaped washer having generally cylindrical cartridge rim, a first end face and a second end face and a semipermeable membrane which is affixed to the first end face of the washer to form an end closure for a cell chamber defined inside of the washer, said sample cartridge being positioned in the cell culture vessel with the rim of the at least one generally cylindrical sample cartridge being positioned in the annular recess so as to separate the front chamber from the back chamber;

a growth of secretor cells in one chamber, and means for collecting secretions from the secretor cells.

17. A cell culture vessel as in claim 16 wherein the semi permeable membrane has pores sized to permit the passage of secretions and prevent the passage of the secretor cells and the secretions are collected in the other chamber.

18. A cell culture vessel as in claim 16 wherein the secretor cells comprise metastasizing tumor cells and the means for collecting secretions comprises target cells in the other chamber.

19. A cell culture vessel as in claim 16 wherein the secretor cells comprise metastasizing tumor cells and the semi permeable membrane carries a reactive agent for selectively binding a chemoattractant stimulating metastasis of the metastasizing tumor cells.

20. A cell culture vessel as in claim 16 wherein the secretor cells comprise metastasizing tumor cells and the semi permeable membrane carries a reactive agent to prevent migration of the metastatic cells into the other chamber.

21. A cell culture vessel as in claim 16 further comprising a chemoattractant substance on the semi-permeable membrane to bind with secretions from the secretor cells.

22. A method for using a bioreactor to produce a bioproduct, said method comprising providing a bioreactor constructed from a front vessel half which define a front chamber, a back vessel half which defines a back chamber, said back chamber being generally cylindrical and having a longitudinal axis, said front vessel half being sealingly engageable with the back vessel half and coming together with said back vessel half so as to form an annular recess for receipt of a cylindrical sample cartridge rim defined by a periphery of a sample cartridge to separate the front chamber from the back chamber, positioning a sample cartridge in the bioreactor, said sample cartridge formed from a generally annularly shaped washer having generally cylindrical cartridge rim, a first end face and a second end face and a semi-permeable membrane which is affixed to the first end face of the washer to form an end closure for a cell chamber defined inside of the washer, said sample cartridge being positioned in the cell culture vessel with the rim of the at least one generally cylindrical sample cartridge being positioned in the annular recess so as to separate the front chamber from the back chamber;

growing secretor cells in one chamber, and collecting secretions from the secretor cells.

23. A method as in claim 22 wherein the semi permeable membrane has pores sized to permit the passage of secretions and prevent the passage of the secretor cells and the secretions are collected in the other chamber.

24. A method as in claim 22 wherein the secretor cells comprises metastasizing tumor cells and the means for collecting secretions comprises target cells in the other chamber.

25. A method as in claim 22 wherein the secretor cells comprise metastasizing tumor cells and the semi permeable membrane carries a reactive agent for selectively binding a chemoattractant stimulating metastasis of the metastasizing tumor cells.

26. A method as in claim 22 wherein the secretor cells comprise metastasizing tumor cells and the semi permeable membrane carries a reactive agent to prevent migration of the metastatic cells into the other chamber.

27. A method as in claim 13 wherein the human cells comprise normal human keratinocytes.

28. A method as in claim 27 wherein the keratinocytes form a confluent monolayer.

29. A method as in claim 28 wherein the keratinocytes are characterized as differentiated and cornified.

30. A method as in claim 13 wherein the human cells comprise human conjunctival epithelium.

31. A method as in claim 13 wherein the human cells comprise human vaginal epithelium.

32. A method as in claim 13 wherein the human cells comprise human cervical epithelium.

33. A method as in claim 13 wherein the human cells comprise human oral cavity epithelium.

34. A method as in claim 13 wherein the human cells comprise human bronchial airway epithelium.

35. A method as in claim 13 wherein the human cells comprise human intestinal epithelium.

36. A method as in claim 13 wherein the human cells comprise human colon epithelium.

37. A method as in claim 13 wherein the human cells comprise human urinary tract epithelium.

38. A method as in claim 13 wherein the human cells comprise human bladder epithelium.

* * * * *